US008672949B2

(12) United States Patent
Griego et al.

(10) Patent No.: US 8,672,949 B2

(45) Date of Patent: Mar. 18, 2014

(54) SELF-ORIENTING POLYPECTOMY SNARE DEVICE

(75) Inventors: John A. Griego, Blackstone, MA (US); Yem Chin, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/415,506

(22) Filed: Mar. 8, 2012

(65) Prior Publication Data

US 2012/0179164 A1 Jul. 12, 2012

Related U.S. Application Data

(63) Continuation of application No. 10/717,775, filed on Nov. 20, 2003, now Pat. No. 8,142,347.

(51) Int. Cl.
*A61B 17/22* (2006.01)

(52) U.S. Cl.
USPC .............................. 606/113; 606/110; 606/47

(58) Field of Classification Search
USPC ................ 606/113, 114, 41, 46, 47, 110, 167
See application file for complete search history.

(56) References Cited

U.S. PATENT DOCUMENTS

| | | | |
|---|---|---|---|
| 1,127,948 | A | 2/1915 | Wappler |
| 2,036,528 | A | 4/1936 | Kesling |
| 2,950,609 | A | 8/1960 | Goodloe |
| 3,554,192 | A | 1/1971 | Isberner |
| 3,895,636 | A | 7/1975 | Schmidt |
| 3,955,578 | A | 5/1976 | Chamness et al. |
| 4,256,113 | A | 3/1981 | Chamness |
| 4,294,254 | A | 10/1981 | Chamness |
| 4,326,530 | A | 4/1982 | Fleury, Jr. |
| 4,327,711 | A | 5/1982 | Takagi |
| 4,345,599 | A | 8/1982 | McCarrell |
| 4,430,083 | A | 2/1984 | Ganz et al. |
| 4,493,320 | A | 1/1985 | Treat |
| 4,503,855 | A | 3/1985 | Maslanka |
| 4,590,938 | A | 5/1986 | Segura et al. |
| 4,593,680 | A | 6/1986 | Kubokawa |
| 4,619,260 | A | 10/1986 | Magill et al. |
| 4,632,110 | A | 12/1986 | Sanagi |

(Continued)

FOREIGN PATENT DOCUMENTS

| | | | |
|---|---|---|---|
| DE | 28 29 159 | 1/1980 | |
| DE | 2829159 A * | 1/1980 | ............. A61B 17/22 |

(Continued)

OTHER PUBLICATIONS

Product Brochure, "Trio 14, Re-engineering Over-the-Wire Balloon Technology," 1994, 4 pages.

*Primary Examiner* — Thomas J Sweet
*Assistant Examiner* — Christopher D Prone
(74) *Attorney, Agent, or Firm* — Seager, Tufte & Wickhem LLC

(57) ABSTRACT

A snare device and methods of making and using the same. The snare device may include a sheath having a proximal end region, a distal end region, and a shaft slidably disposed therein. A handle may be coupled to the shaft and disposed adjacent the proximal end region. The snare device may also include a swivel disposed adjacent the distal end region of the sheath and coupled to the shaft and to a snare loop.

20 Claims, 4 Drawing Sheets

(56) References Cited

U.S. PATENT DOCUMENTS

| | | | |
|---|---|---|---|
| 4,706,656 | A | 11/1987 | Kuboto |
| 4,763,668 | A | 8/1988 | Macek et al. |
| 4,785,825 | A | 11/1988 | Romaniuk et al. |
| 4,790,831 | A | 12/1988 | Skribiski |
| D301,614 | S | 6/1989 | Kozak et al. |
| 4,840,176 | A | 6/1989 | Ohno |
| 4,840,623 | A | 6/1989 | Quackenbush |
| 4,869,238 | A | 9/1989 | Opie et al. |
| 4,872,456 | A | 10/1989 | Hasson |
| 4,875,718 | A | 10/1989 | Marken |
| 4,905,691 | A | 3/1990 | Rydell |
| 4,945,920 | A | 8/1990 | Clossick |
| 4,950,232 | A | 8/1990 | Ruzicka et al. |
| 4,967,732 | A | 11/1990 | Inoue |
| 4,973,321 | A | 11/1990 | Michelson |
| 5,005,755 | A | 4/1991 | Takahashi et al. |
| 5,026,371 | A | 6/1991 | Rydell et al. |
| 5,059,199 | A | 10/1991 | Okada et al. |
| 5,066,295 | A | 11/1991 | Kozak et al. |
| 5,084,054 | A | 1/1992 | Bencini et al. |
| 5,114,403 | A | 5/1992 | Clark et al. |
| 5,125,909 | A | 6/1992 | Heimberger |
| 5,129,913 | A | 7/1992 | Ruppert |
| 5,147,316 | A | 9/1992 | Castillenti |
| 5,147,373 | A | 9/1992 | Ferzli |
| RE34,110 | E | 10/1992 | Opie et al. |
| 5,156,590 | A | 10/1992 | Vilmar |
| 5,158,561 | A | 10/1992 | Rydell et al. |
| 5,163,942 | A | 11/1992 | Rydell |
| 5,176,677 | A | 1/1993 | Wuchinich |
| 5,176,702 | A | 1/1993 | Bales et al. |
| 5,179,935 | A | 1/1993 | Miyagi |
| 5,183,470 | A | 2/1993 | Wetterman |
| 5,201,740 | A | 4/1993 | Nakao et al. |
| 5,201,743 | A | 4/1993 | Haber et al. |
| 5,244,619 | A | 9/1993 | Burnham |
| 5,254,117 | A | 10/1993 | Rigby et al. |
| 5,254,130 | A | 10/1993 | Poncet et al. |
| 5,279,280 | A | 1/1994 | Bacich et al. |
| 5,281,220 | A | 1/1994 | Blake, III |
| 5,281,230 | A | 1/1994 | Heidmueller |
| 5,290,294 | A | 3/1994 | Cox et al. |
| 5,318,564 | A | 6/1994 | Eggers |
| 5,334,169 | A | 8/1994 | Brown et al. |
| 5,336,227 | A | 8/1994 | Nakao et al. |
| 5,358,493 | A | 10/1994 | Schweich, Jr. |
| 5,376,094 | A | 12/1994 | Kline |
| 5,403,342 | A | 4/1995 | Tovey et al. |
| 5,404,887 | A | 4/1995 | Prather |
| 5,406,939 | A | 4/1995 | Bala |
| 5,439,478 | A | 8/1995 | Palmer |
| 5,465,710 | A | 11/1995 | Miyagi |
| 5,486,182 | A | 1/1996 | Nakao et al. |
| 5,496,292 | A | 3/1996 | Burnham |
| 5,501,692 | A | 3/1996 | Riza |
| 5,542,948 | A | 8/1996 | Weaver et al. |
| 5,584,843 | A | 12/1996 | Wulfman et al. |
| 5,588,964 | A | 12/1996 | Imran et al. |
| 5,591,202 | A | 1/1997 | Slater et al. |
| 5,601,533 | A | 2/1997 | Hancke et al. |
| 5,647,846 | A | 7/1997 | Berg et al. |
| 5,681,296 | A | 10/1997 | Ishida |
| 5,718,360 | A | 2/1998 | Green et al. |
| 5,741,271 | A | 4/1998 | Nakao et al. |
| 5,746,747 | A | 5/1998 | McKeating |
| 5,755,724 | A | 5/1998 | Yoon |
| 5,759,187 | A | 6/1998 | Nakao et al. |
| 5,762,631 | A | 6/1998 | Klein |
| 5,766,217 | A | 6/1998 | Christy |
| 5,769,841 | A | 6/1998 | Odell et al. |
| 5,792,116 | A | 8/1998 | Berg et al. |
| 5,800,444 | A | 9/1998 | Ridinger et al. |
| 5,814,052 | A | 9/1998 | Nakao et al. |
| 5,817,111 | A | 10/1998 | Riza |
| 5,820,464 | A | 10/1998 | Parlato |
| 5,827,177 | A | 10/1998 | Omeda et al. |
| 5,827,272 | A | 10/1998 | Breining et al. |
| 5,846,248 | A | 12/1998 | Chu et al. |
| 5,860,975 | A | 1/1999 | Goble et al. |
| 5,882,347 | A | 3/1999 | Mouris-Laan |
| 5,885,508 | A | 3/1999 | Ishida |
| 5,906,620 | A | 5/1999 | Nakao et al. |
| 5,906,621 | A | 5/1999 | Secrest et al. |
| 5,957,932 | A | 9/1999 | Bates et al. |
| 5,961,511 | A | 10/1999 | Mortier et al. |
| 5,971,994 | A | 10/1999 | Fritzsch |
| 5,984,904 | A | 11/1999 | Steen et al. |
| 5,984,920 | A | 11/1999 | Steinbach |
| 5,989,247 | A | 11/1999 | Chambers |
| 5,993,474 | A | 11/1999 | Ouchi |
| 6,001,096 | A | 12/1999 | Bissinger et al. |
| 6,010,512 | A | 1/2000 | Chu et al. |
| 6,015,381 | A | 1/2000 | Ouchi |
| 6,015,415 | A | 1/2000 | Avellanet |
| 6,024,708 | A | 2/2000 | Bales et al. |
| 6,027,460 | A | 2/2000 | Shturman |
| 6,050,995 | A | 4/2000 | Durgin |
| 6,068,603 | A | 5/2000 | Suzuki |
| 6,071,233 | A | 6/2000 | Ishikawa et al. |
| 6,074,408 | A | 6/2000 | Freeman |
| 6,090,073 | A | 7/2000 | Gill |
| 6,090,129 | A | 7/2000 | Ouchi |
| 6,093,195 | A | 7/2000 | Ouchi |
| 6,235,026 | B1 | 5/2001 | Smith |
| 6,299,612 | B1 | 10/2001 | Ouchi |
| 6,517,539 | B1 | 2/2003 | Smith et al. |
| 6,530,899 | B1 | 3/2003 | Savage |
| 6,537,205 | B1 | 3/2003 | Smith |
| 2002/0010485 | A1 * | 1/2002 | Griego et al. ................. 606/167 |
| 2002/0151889 | A1 | 10/2002 | Swanson et al. |

FOREIGN PATENT DOCUMENTS

| | | |
|---|---|---|
| DE | 36 16 193 | 11/1986 |
| DE | 199 53 359 | 5/2000 |
| WO | WO 92/22254 | 12/1992 |
| WO | WO 00/42926 | 7/2000 |
| WO | WO 00/53107 | 9/2000 |
| WO | WO 01/10321 | 2/2001 |

* cited by examiner

SELF-ORIENTING POLYPECTOMY SNARE DEVICE

RELATED APPLICATIONS

This application is a continuation of U.S. application Ser. No. 10/717,775, filed Nov. 20, 2003, now U.S. Pat. No. 8,142,347, the entire disclosure of which is incorporated herein by reference.

FIELD OF THE INVENTION

The present invention pertains to a snare device for insertion in a body lumen for removal of a tissue growth, such as a polyp. More particularly, the present invention pertains to such a snare device that includes a self-orienting snare loop.

BACKGROUND OF THE INVENTION

Polypectomy snare instruments are used for the endoscopic removal of hypertrophic tissue growths within a body cavity, and particularly within the colon. Polypectomy snare instruments generally include an elongate tubular member, such as a catheter sheath, a shaft extending through the tubular member, a wire forming a snare (loop) at the distal end of the shaft, and a handle for moving the shaft distally and proximally within the tubular member. The snare can be opened by moving the snare beyond the distal end of the sheath and closed by retraction of the snare into the tubular member, each effected by movement of the shaft relative to the sheath. A number of different types of snare devices exist, each having certain advantages and disadvantages. There is an ongoing need for refined snare devices.

SUMMARY OF THE INVENTION

The invention provides design, material, and manufacturing method alternatives for medical devices, for example, snare devices. In at least some embodiments, the snare devices include a sheath having a proximal end region, a distal end region, and a shaft slidably disposed therein. A handle may be coupled to the shaft and disposed adjacent the proximal end region of the sheath. The snare device may also include a swivel disposed adjacent the distal end region of the sheath and coupled to the shaft and to a snare loop. These and some of the other features and characteristics of example embodiments are described in more detail below.

DETAILED DESCRIPTION OF THE PREFERRED EMBODIMENTS

Figure 1:
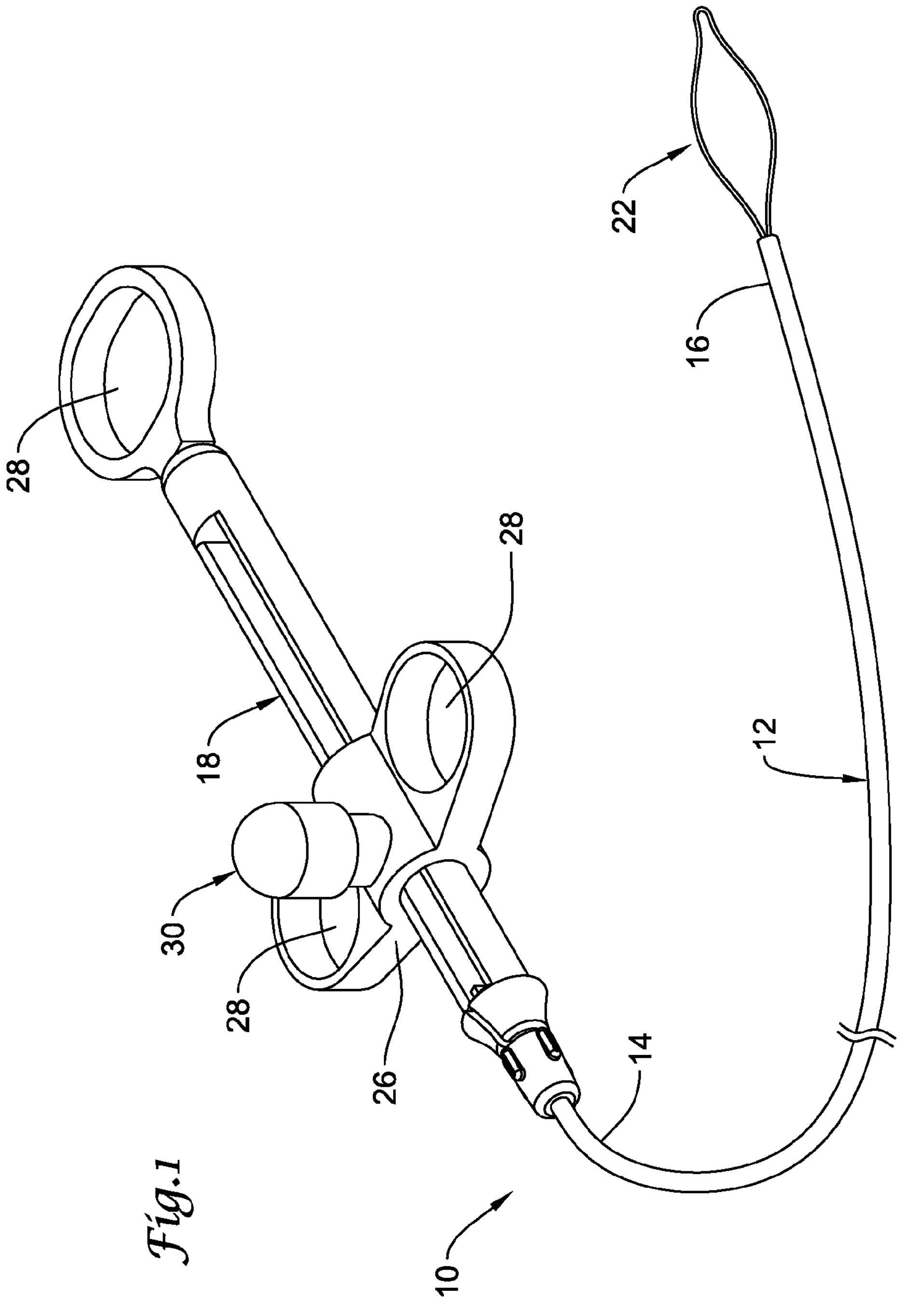
FIG. 1 is a perspective view of an example snare device.

The following description should be read with reference to the drawings wherein like reference numerals indicate like elements throughout the several views. The detailed description and drawings illustrate example embodiments of the claimed invention.

Figure 2:
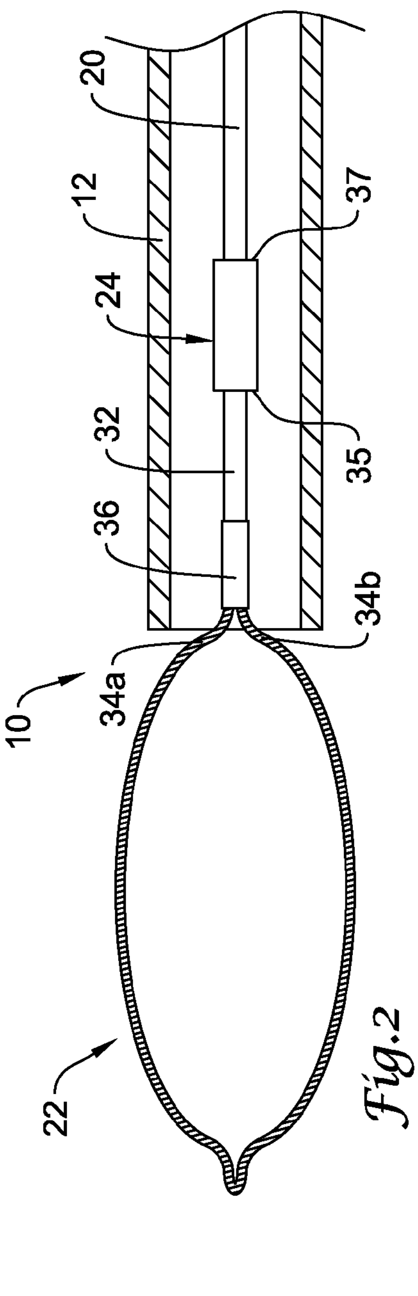
FIG. 2 is a partial cross-sectional side view of an example snare device.

FIG. 1 illustrates an example snare device 10. Snare device 10 may include an elongate sheath 12 having a proximal end region 14 and a distal end region 16. A handle 18 may be coupled to the proximal end region 14. A shaft member 20 may be disposed within at least a portion of sheath 12 and be slidable therein. A snare loop 22 may be coupled to shaft member 20, for example, by a swivel 24 (shaft member 20 and swivel 24 are not shown in FIG. 1, but are seen in FIG. 2). Swivel 24 allows snare loop 22 to be rotated independently of the rotation of shaft member 20. Accordingly, when snare loop 22 is used, for example to excise a polyp, the interaction of snare loop 22 with the polyp can result in rotation of snare loop 22 so that it can orient itself in a position for excising the polyp. The appropriate position may be, for example, snare loop 22 disposed over and surrounding the polyp and disposed adjacent the base of the polyp. Thus, snare loop 22 is understood to be "self-orienting", or in other words, capable of properly orienting itself relative to a polyp without the user needing to manipulate handle 18, shaft member 20, or some other proximally-disposed portion of snare device 10 to mechanically rotate snare loop 22 by manipulating handle 18.

By including a self-orienting snare loop 22, snare device 10 may be desirable over other types of snare devices. For example, rotation of typical snares usually includes rotating a shaft or cable at the proximal handle that extends along essentially the entire length of the snare device. Thus, the rotation of the snare loop in these types of devices is dependent on the ability of the rotational forces applied to the cable at the handle (or some other proximal position) to transmit down the length of the device. Because the device may be disposed along a tortuous and sometimes lengthy path, rotation may not efficiently transmit. This could result in a "whipping effect" where the snare loop rapidly rotates with little or no control of the position of the loop. Moreover, these types of devices require that the shaft or cable used to rotate the snare loop be capable of transmitting torque. Therefore, the cable might need to have an increased outside diameter (which could increase the profile of the device) and to be sufficiently torque-transmitting (which could increase the manufacturing complexity and/or manufacturing costs).

Accordingly, in a preferred embodiments of snare device 10 there is included a swivel 24, which allows snare loop 22 to rotate independently of shaft 20 or with respect to shaft 20. In general, swivel 24 may be positioned adjacent to distal end region 16 of sheath 12 so that only a relatively short length of material rotates when snare loop 22 rotates. However, it may be desirable for swivel 24 to be set back proximally a distance so that even when snare loop 22 is configured for severing a polyp (i.e., when snare loop 22 extends distally from sheath 12), swivel 24 still remains within sheath 12. This embodiment may help reduce the possibility that swivel 24 may catch or become "hung up" on sheath 12 when snare loop 22 is proximally refracted.

The exact form of swivel 24 may vary and can include essentially any suitable form or type of swivel. Some examples of suitable swivels are described below and illustrated in FIGS. 4-6. These and other swivels including barrel swivels, ball and socket swivels, prismatic swivels (e.g., dodecahex swivels, large sqocta swivels, and small sqocta swivels), conic swivels (e.g., octonic swivels, pentonic swivels, and sqonic swivels), and the like, or any other suitable swiveling device are contemplated. It can be appreciated that a number of different swivels or swiveling means can be used without departing from the spirit of the invention.

Sheath 12 may be made from any suitable material including polymers, metals, metal alloys, metal-polymer composites, and the like. Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, sheath 12 can be blended with a liquid crystal polymer (LCP). For example, the mixture can contain up to about 5% LCP. By employing selection of materials and processing techniques, thermoplastic, solvent soluble, and thermosetting variants of these and other materials can be employed to achieve the desired results.

Shaft 20 may be made from any suitable material including polymers, metals, metal alloys, metal-polymer composites, and the like. Some examples of suitable polymers include any of those listed above. Some examples of suitable metals and metal alloys include stainless steel, such as 304V, 304L, and 316L stainless steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Sheath 12, shaft 20, portions thereof, or other components of snare device 10 may also be doped with or otherwise include a radiopaque material. Radiopaque materials are understood to be materials capable of producing a relatively bright image on a fluoroscopy screen or another imaging technique during a medical procedure. This relatively bright image aids the user of snare device 10 in determining its location. Some examples of radiopaque materials can include, but are not limited to, gold, platinum, palladium, tantalum, tungsten alloy, plastic material loaded with a radiopaque filler, and the like. Alternatively, sheath 12 or other components of snare device 10 may include other known marker bands, radiopaque coils, and the like.

Handle 18 may be made from any suitable material including any of those listed herein. Handle 18 may be disposed at proximal end region 14 of sheath 12 and be connected to (or adjacent) the proximal end of shaft 20. In general, handle 18 may serve as a graspable surface for device 10 and may be used to longitudinally move snare loop 22 relative to sheath 12. For example, handle 18 may include a sliding portion 26 that is attached to shaft 20 so that movement of sliding portion 26 (either distally or proximally) results in shaft 20 moving in the same longitudinal direction. Snare device 10 may be configured so that when sliding portion 26 and shaft 20 are slid or positioned distally (as shown in FIG. 1), snare loop 22 may extend distally from sheath 12, where it is in a position for capturing and removing polyps. When sliding portion 26 and shaft 20 are slid or positioned proximally, snare loop 22 may be substantially collapsed and disposed within sheath 12.

Handle 18 may include a number of other structural features. For example, one or more finger holes 28 may be coupled to handle 18 and/or sliding portion 26 to help assist movement of sliding portion 28. Handle 18 may also include a port 30. Port 30 may be used, for example, as an access point to apply and/or deliver cautery current (including mono-polar and bipolar current) to shaft 20 and/or snare loop 22. It can be appreciated that a number of alterations can be made to the configuration and features of handle 18 without departing from the spirit of the invention.

In use, snare device 10 may be configured by proximally positioning sliding portion 26 of handle 18 so that snare loop 22 is collapsed and disposed within sheath 12. Device 10 can then be advanced through a body lumen to a suitable target location. In at least some embodiments, advancing device 10 may include passing sheath 12 through the working channel of an endoscope. Once inside the body lumen, sliding portion 26 can be slid distally to activate snare loop 22, whereby loop 22 emerges and becomes positioned distally of sheath 12. As snare loop 22 contacts the surface of the target site (e.g., a polyp) and a slight pressure is exerted, loop 22 can rotate about swivel 24 to the suitable position for "capturing" the polyp. In some instances, additional pressure may be used to lay snare loop 22 flat at the base of the polyp. When properly oriented, snare loop 22 can be retracted by proximally moving sliding portion 26. As loop 22 engages the distal end region 16 of sheath 12, the opening of loop 22 may reduce in size, thereby "squeezing" and, ultimately, severing the polyp from the body. In some embodiments, cautery current (including mono-polar and bipolar current) can be applied (e.g., at port 30 so that current flows along shaft 20 and into snare loop 22, which may help cauterize the area adjacent the newly severed polyp. After the appropriate number of polyps are severed, device 10 can be removed from the body.

Figure 3:
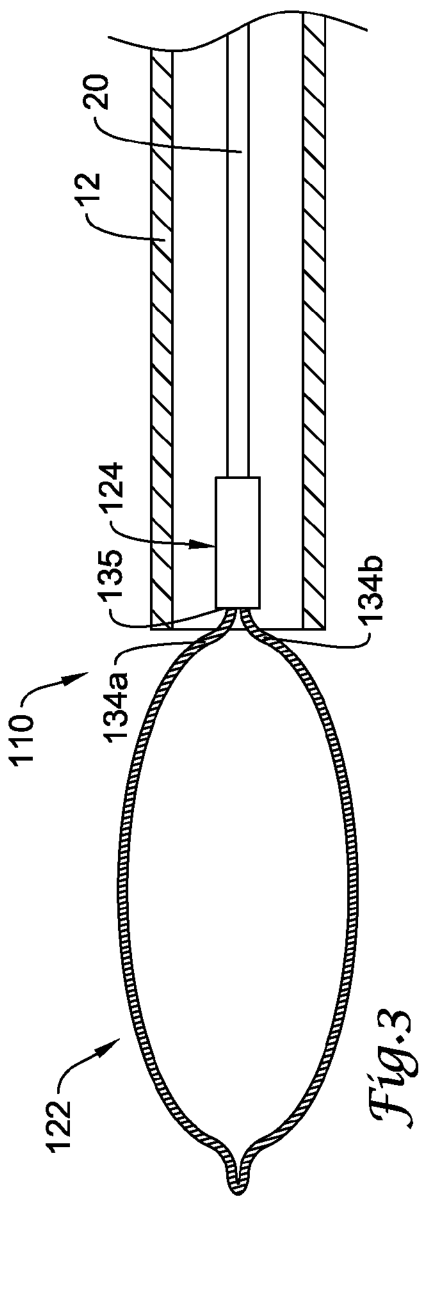
FIG. 3 is a partial cross-sectional side view of another example snare device.

The arrangement of shaft 20 relative to swivel 24 and snare loop 22 may vary. For example, FIG. 2 is a partial cross-sectional side view of device 10, showing swivel 24 disposed between shaft 20 and a linking shaft 32. According to this embodiment, the proximal leg regions or legs 34 (in FIG. 2 there are two legs indicated by reference numbers **34*a* and 34*b*) of snare loop 22 converge at and are connected to one another by a connector 36. Connector 36 is then connected to linking shaft 32, which extends to swivel 24. Accordingly, a first end region 35 of swivel 24 is connected to linking shaft 32 and a second end region 37 of swivel 24 is connected to shaft 12. In contrast, FIG. 3 illustrates snare device 110, where legs 134*a*/134*b* of snare loop 122 are coupled directly to first end region 135 of swivel 124**.

Figure 4:
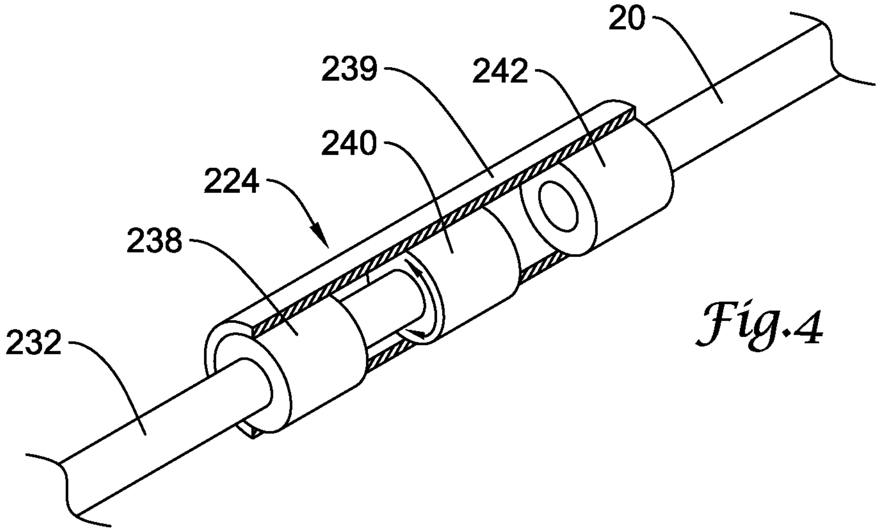
FIG. 4 is a partial cross-sectional perspective view of an example swivel for use with a snare device.

FIGS. 4-7 illustrate examples of suitable swivels that may be utilized with any of the snare devices disclosed herein. For the purpose of simplicity, these figures depict a single shaft (e.g., shaft 232 as shown in FIG. 4) coupled to the distal end of the swivel. However, this single shaft is intended to represent embodiments where linking shaft 32 is used as well as when legs **34*a*/34*b* (or legs 134*a*/134*b*) are directly attached to the swivel. For example, FIG. 4 shows swivel 224 having a swivel body 239. One or more bearings, for example a first bearing 238, second bearing 240, and a third bearing 242, may be disposed within swivel body 239. Shaft 232 may extend through bearing 238 and be slidable and/or moveable therein. Second bearing 240 may be coupled to the end of shaft 232 so as to prevent shaft 232 coming out of or otherwise disassociating from swivel 224. First bearing 238 may be fixed to body 239 and second bearing 240 may be rotatable within swivel body 239. According to this embodiment, shaft 232 (and, ultimately, snare loop 22) is rotatable by virtue of shaft 232 and second bearing 240 rotating as indicated by the arrow on bearing 240. Shaft 20 may be connected to third bearing 242. In some embodiments, third bearing 242 may be fixed to swivel body 239**.

Figure 5:
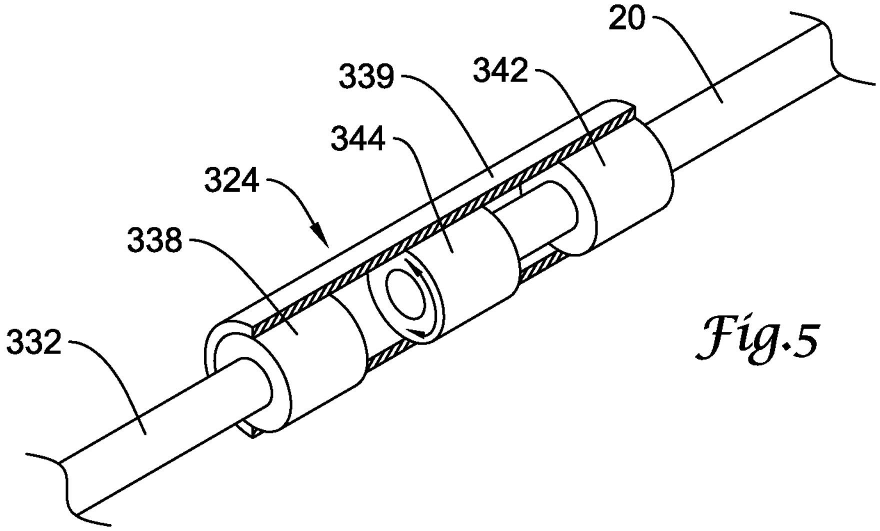
FIG. 5 is a partial cross-sectional perspective view of another example swivel for use with a snare device.

In other embodiments, such as the one illustrated in FIG. 5, essentially the opposite arrangement may be used. For example, swivel 324 may include swivel body 339, bearing 338, bearing 342 and another bearing 344. Shaft 332 may be connected to fixed bearing 338. Shaft 332 may be rotatable by virtue of swivel body 339 rotating about bearing 344 and shaft 20.

Figure 6:
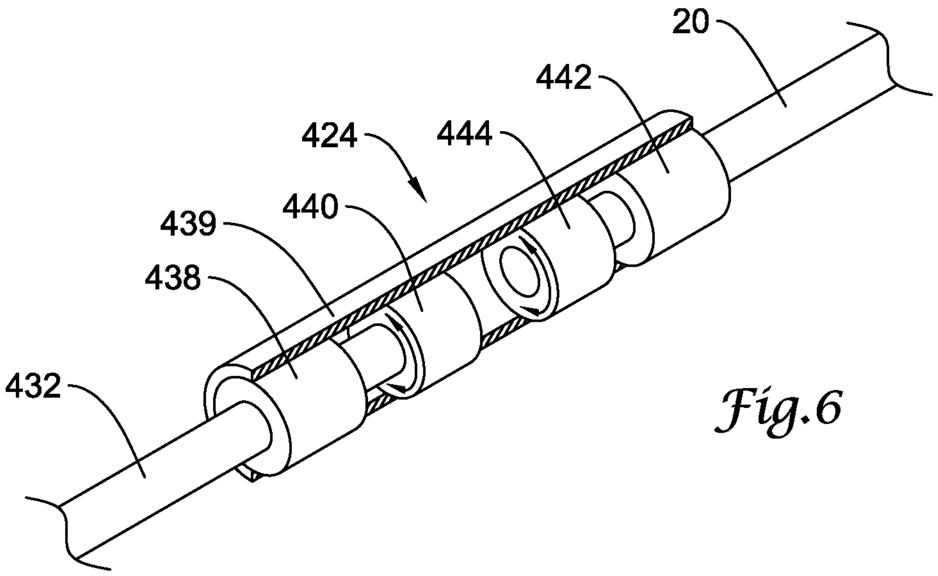
FIG. 6 is a partial cross-sectional perspective view of another example swivel for use with a snare device.

FIG. 6 depicts another swivel 424 where both shaft 432 and shaft 20 are rotatable within swivel body 439. According to this embodiment, shaft 432 extends through bearing 438 and is connected to rotatable bearing 440. Similarly, shaft 20 extends through bearing 442 and is connected to bearing 444. By virtue of both shaft 432 and shaft 20 being configured to be rotatable, it can be appreciated that snare loop 22 can rotate independently of shaft 20.

Figure 7:
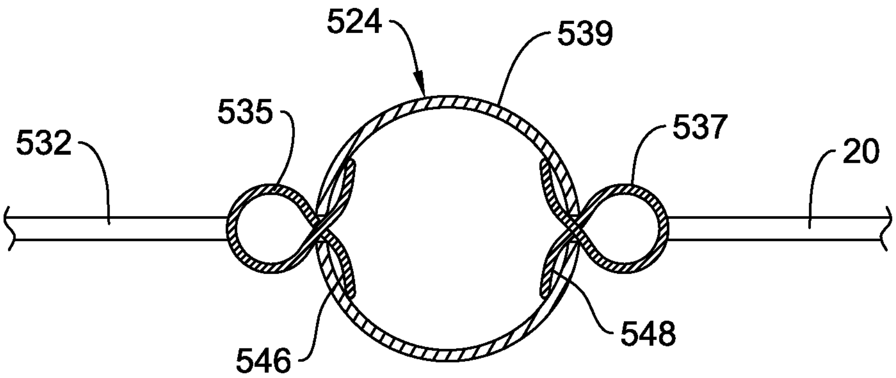
FIG. 7 is a partial cross-sectional perspective view of another example swivel for use with a snare device.

Another swivel 524 is shown in FIG. 7. Swivel 524 represents an example of a barrel swivel, which may be similar to the type of swivel commonly used by anglers to connect a hook, leader, or fishing lure to the end of a fishing line. Swivel 524 may include swivel body 539, first end region 535, a first stop or stopping member 546 disposed adjacent first end region 535, second end region 537, and a second stop or stopping member 548 disposed adjacent second end region 537. In general, one or both of stopping members 546/548 may be configured to be rotatable within swivel body 539 while preventing end regions 535/537 from becoming disassociated from swivel body 539. Shaft 532 may be coupled to first end region 535 and, thus, be rotatable. In some embodiments, shaft 20 is connected to second end region 537 and may (in addition to or as an alternative to the rotation of shaft 532) be rotatable.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A self-orienting snare loop device, comprising:
an elongate tubular member;
a shaft slidably disposed within the tubular member, the shaft having a distal end;
a swivel attached to the distal end of the shaft;
wherein the swivel includes a cylindrical swivel body with a constant inner diameter;
a linking member attached to the swivel body and extending distally therefrom; and
a snare loop including a pair of legs, wherein each of the legs is attached to the linking member; and
wherein the snare loop is capable of self-orienting itself relative to a target tissue independently of linear movement of the linking member.

2. The self-orienting snare loop device of claim 1, wherein the shaft is configured to shift between a first configuration where a distal end of the snare loop is disposed proximally of a distal end of the tubular member and a second configuration where a proximal end of the snare loop is disposed distally of the distal end of the tubular member.

3. The self-orienting snare loop device of claim 1, wherein a first bearing is disposed within the swivel body.

4. The self-orienting snare loop device of claim 3, wherein the first bearing is attached to the shaft.

5. The self-orienting snare loop device of claim 3, wherein the first bearing is attached to the linking member.

6. The self-orienting snare loop device of claim 3, wherein a second bearing is disposed within the swivel body.

7. The self-orienting snare loop device of claim 6, wherein the first bearing is attached to the shaft and the second bearing is attached to the linking member.

8. The self-orienting snare loop device of claim 6, wherein a third bearing is disposed within the swivel body.

9. The self-orienting snare loop device of claim 8, wherein the first bearing is attached to the swivel body, wherein the shaft extends through the first bearing and is attached to the second bearing, and wherein the linking member is attached to the third bearing.

10. The self-orienting snare loop device of claim 8, wherein a fourth bearing is disposed within the swivel body.

11. The self-orienting snare loop device of claim 10, wherein the first bearing is attached to the swivel body, wherein the shaft extends through the first bearing and is attached to the second bearing, wherein the third bearing is attached to the swivel body, and wherein the linking member extending through the third bearing and is attached to the fourth bearing.

12. The self-orienting snare loop device of claim 1, wherein a first connector having a first end region attached to the shaft and a first stop region disposed within the swivel body, and a second connector having a second end region attached to the linking member and a second stop region disposed within the swivel body.

13. A self-orienting snare loop device, comprising:
an elongate tubular sheath;
a shaft slidably disposed within the sheath, the shaft having a distal end;
a swivel with a constant inner diameter attached to the distal end of the shaft and positioned within the sheath;
a self-orienting snare loop coupled to the swivel, where the self-orienting snare loop is capable of self-orienting itself relative to a target tissue independently of linear movement of the snare loop; and
wherein the shaft is configured to shift between a first configuration where a distal end of the snare loop is disposed proximally of a distal end of the tubular member and a second configuration where a proximal end of the snare loop is disposed distally of the distal end of the tubular member.

14. The self-orienting snare loop device of claim 13, wherein the snare loop include a pair of legs that are attached to a linking shaft, and wherein the linking shaft is attached to the swivel.

15. The self-orienting snare loop of claim 13, wherein the snare loop is independently rotatable relative to the swivel.

16. The self-orienting snare loop of claim 13, wherein the shaft is independently rotatable relative to the swivel.

17. The self-orienting snare loop of claim 13, wherein both the snare loop and the shaft are independently rotatable relative to the swivel.

18. A method for removing a polyp, the method comprising:
providing a self-orienting snare loop device, the device including:
an elongate tubular member;
a shaft slidably disposed within the tubular member, the shaft having a distal end;

a swivel with a constant inner diameter attached to the distal end of the shaft;

a linking member attached to the swivel and extending distally therefrom; and a snare loop including a pair of legs, wherein each of the legs is attached to the linking member; and wherein the snare loop is capable of self-orienting itself relative to a target tissue independently of linear movement of the linking member;

advancing the tubular member through a body lumen to a position adjacent a polyp;

distally advancing the shaft out from the tubular member;

engaging the polyp with the snare loop, wherein engaging the polyp with the snare loop causes the snare loop to rotate and orient itself about the polyp; and proximally retracting the snare loop into the sheath, thereby cutting the polyp.

19. The method of claim 18, wherein the shaft is configured to shift between a first configuration where a distal end of the snare loop is disposed proximally of a distal end of the tubular member and a second configuration where a proximal end of the snare loop is disposed distally of the distal end of the tubular member, and wherein distally advancing the shaft out from the tubular member includes shifting the shaft from the first configuration to the second configuration.

20. The method of claim 18, further comprising delivering current to the snare loop.

* * * * *